(12) United States Patent
Nicora et al.

(10) Patent No.: US 6,926,509 B2
(45) Date of Patent: Aug. 9, 2005

(54) APPARATUS FOR EXTRUDING TUBING HAVING A VARIABLE WALL THICKNESS

(75) Inventors: Scott W. Nicora, St. Petersburg, FL (US); Geary A. Havran, Tampa, FL (US)

(73) Assignee: NDH Medical, Inc., St. Petersburg, FL (US)

( * ) Notice: Subject to any disclaimer, the term of this patent is extended or adjusted under 35 U.S.C. 154(b) by 319 days.

(21) Appl. No.: 10/159,652

(22) Filed: May 31, 2002

(65) Prior Publication Data

US 2003/0222369 A1 Dec. 4, 2003

(51) Int. Cl.$^7$ ............................................. B29C 47/22
(52) U.S. Cl. ........................ 425/135; 425/380; 425/465; 425/466
(58) Field of Search .............................. 425/380, 381, 425/465, 466, 135

(56) References Cited

U.S. PATENT DOCUMENTS

| | | | |
|---|---|---|---|
| 2,044,961 A | * 6/1936 | Waner | 425/465 |
| 3,147,515 A | 9/1964 | Amsden | |
| 3,209,404 A | * 10/1965 | Hagen | 425/466 |
| 3,649,148 A | * 3/1972 | Waltman et al. | 425/466 |
| 3,753,636 A | * 8/1973 | Waterloo | 425/465 |
| 4,036,930 A | 7/1977 | Murai et al. | |
| 4,171,193 A | 10/1979 | Rahlfs | |
| 4,171,195 A | * 10/1979 | Klein et al. | 425/466 |
| 4,432,718 A | * 2/1984 | Wurzer | 425/466 |
| 4,528,832 A | 7/1985 | Fuchs, Jr. | |
| 4,563,147 A | * 1/1986 | Langecker | 425/466 |
| 5,057,267 A | * 10/1991 | Seizert et al. | 425/465 |
| 5,472,418 A | 12/1995 | Palestrant | |
| 5,511,965 A | 4/1996 | Batdorf et al. | |
| 5,618,267 A | 4/1997 | Palestrant | |
| 5,945,052 A | * 8/1999 | Schryver et al. | 425/465 |
| 6,024,557 A | * 2/2000 | Feuerherm | 425/465 |
| 6,284,168 B1 | * 9/2001 | Robinson | 264/40.1 |
| 6,394,141 B2 | * 5/2002 | Wages et al. | 138/115 |
| 2001/0027818 A1 | 10/2001 | Wages et al. | |

FOREIGN PATENT DOCUMENTS

| | | |
|---|---|---|
| FR | 1 289 838 A | 4/1962 |
| JP | 55144130 | 10/1980 |
| WO | WO 00/21730 A | 4/2000 |

* cited by examiner

Primary Examiner—James P. Mackey
(74) Attorney, Agent, or Firm—Roger M. Rathbun

(57) ABSTRACT

An extruder apparatus and method for producing an extruded tubing having varying inner dimensions without changing the outer dimensions. The tubing is forced from the die face of an extrusion head having an extruder die and an internal mandrel determining the outer and inner dimensions, respectively, of the extruded tubing. The outer dimensions of the mandrel varied by the user to change the inner dimensions of the extruded tubing. A pressure is maintained in the extruded tubing to prevent its collapse and that pressure is changed based upon the change of the external dimensions of the mandrel and the wall thickness of the tubing. In one embodiment, the mandrel is comprised of a core and a plurality of telescoping sleeves. Each sleeve is movable between a retracted position where the sleeve is displaced away from the die face and an extended position where sleeve is at the die face. There may be multiple mandrels in the case of multi-lumen catheters.

9 Claims, 6 Drawing Sheets

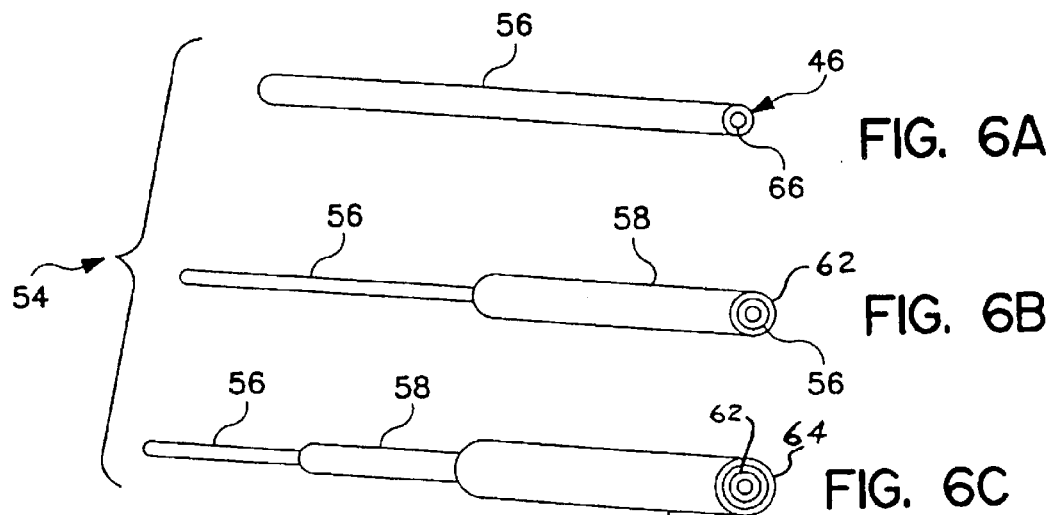
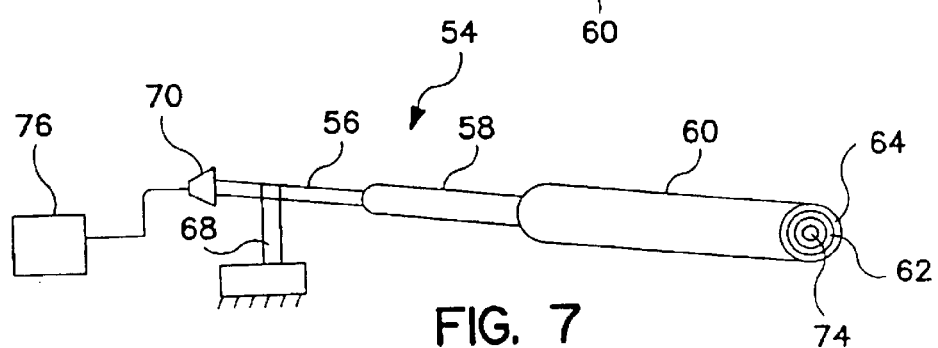
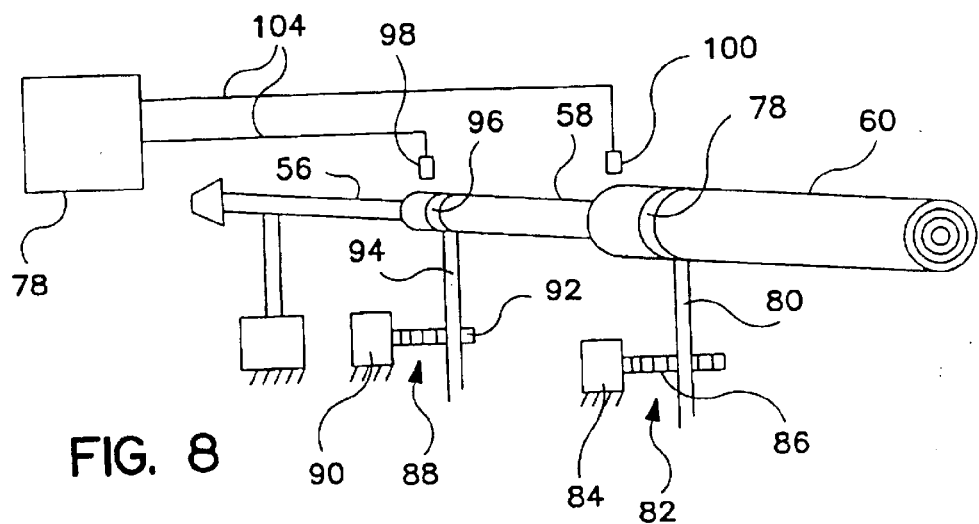

APPARATUS FOR EXTRUDING TUBING HAVING A VARIABLE WALL THICKNESS

BACKGROUND

The present invention relates to an apparatus and method for the extrusion of tubing, and, more particularly, to an apparatus and method for extruding a tubing having an variable wall thickness by varying its inner dimensions.

There are, of course, many well known and established methods and apparatus used in the extrusion of tubing, particularly plastic tubing, many of which are utilized for extruding such tubing that is to be used for medical purposes, such as in the production of catheters and the like.

Typical of such extrusions include the production of multi-lumen catheters and special purpose catheters that are custom extruded for a particular medical purpose. One need, however, is for the production by the extrusion process of a catheter having a relatively constant outer dimension but where the inner dimension can be varied so that such inner dimension can be selectively designed and manufactured by the extruder to have a varying, but predetermined dimension.

In U.S. Pat. No. 5,511,965 of Batdorf et al, there is disclosed an apparatus for the production of an extruded tubing where the inner diameter is kept relatively constant but where the outer diameter can be varied. In that patent, extrudable material is forced around a mandrel having a constant diameter, thereby establishing a constant inner diameter, but the outer die aperture is varied as desired in order to vary the outer diameter between a minimum outer diameter and a maximum outer diameter as desired by the operator.

While useful for the intended purpose, the apparatus of Batdorf et al is not applicable to the production of extruded tubing where the outer dimension is held to be relatively constant while the inner dimension is selectively varied in a predetermined manner as the extruded tubing is formed.

Accordingly, it would be advantageous to have an apparatus that could produce an extruded tubing having relatively constant outer dimensions while having the ability to vary the inner dimensions as desired by the operator in order to produce a particular specialized tubing, especially manufactured for medical use, but which is certainly also applicable to non-medical uses.

SUMMARY OF THE INVENTION

Accordingly, the present invention relates to an apparatus and method of extruding a tubing of a thermoplastic or thermosetting material. The present apparatus and method is applicable to a wide variety of tubing, including those having an outer peripheral surface in the configuration of a circle, square, rectangle, hexagon or any other of a wide variety of such configurations that can be extruded for a myriad of purposes. Thus by "tubing" as used herein, the term is intended to cover any of the foregoing external peripheral surfaces as well as other surfaces that can be extruded using the present invention. Tubing, can, as used herein, also describe not only the foregoing variety of external surfaces but also is applicable as well to single lumen tubing and multi-lumen tubing where the individual lumens of a multi-lumen catheter may, themselves, have differing configurations.

Accordingly, in accordance with the present invention, there is provided an apparatus and a method for extruding a tubing where the exterior dimension or dimensions of the tubing remain constant while the internal dimension or dimensions can be varied, thereby creating a tubing having a selectively varying wall thickness.

In carrying out the present invention, there is an extruder that has a specially constructed extrusion head that allows the user to vary the internal dimensions of the tubing as that tubing is extruded and formed. The internal dimensions of the tubing are basically established by a mandrel over which the material to be extruded flows and the distal end of the mandrel is located at or near the die face where the material emerges from the extrusion head during the formation of the tubing, that is, the die face is in plane generally at a right angle to the flow of the material, or to the longitudinal axis of the mandrel, and is at the very end of the extrusion head. As such, the material flowing outwardly through the die face assumes the dimensions of the mandrel for its internal dimensions and the die for its external dimensions.

Thus, with the present invention, the exterior dimensions of the mandrel can be varied by the user in accordance with the desired internal dimensions of the extruded tubing such that the user can predetermine those internal dimensions and still change such dimensions during the course of the extrusion process itself. Since, with the present invention, the outer dimensions or dimension are not variable, it can be seen that the wall thickness of the tubing can be varied by the user to produce a varying wall thickness of the tubing.

In the preferred embodiment, the mandrel comprises a core which basically establishes the maximum wall thickness, or smallest internal dimensions of the extruded tubing and there is at least one sleeve, and preferably a plurality of sleeves that are mounted coaxial and exterior of the core and those sleeves are telescoped together such that each sleeve can be moved from a retracted position where the sleeve is displaced away from the die face and therefore does not have an effect on the inner dimensions of the extruded tubing and an extended position where the sleeve is located at the die face of the extrusion head and therefore does control the inner dimensions of the extruded tubing.

When a plurality of sleeves are employed, the sleeves are progressively movable to the extended position starting with the smaller of the sleeves and working outwardly to the larger of the sleeves. Thus, by moving a sleeve from its retracted position to its extended position at the die face, the inner dimensions of the tubing can be varied and that is true with respect to the other sleeves.

The present invention can also readily be employed in the extrusion of multiple lumen tubing and catheters and, with such embodiment, the extruder can have an extrusion head having a plurality of mandrels interfitted therein and where one or more of such mandrels is constructed so as to be capable of varying the external dimension as will be hereinafter explained and described. As such, a multilumen catheter can be extruded where any one or more of the lumens can utilize the present invention so as to have the internal dimensions of any particular lumen or lumens vary as desired by the user by changing the external dimensions of one or more mandrels.

In the preferred embodiment, there is also a motive system that can automatically move the sleeves between the retracted and the extended positions so that the user can automatically or manually select and vary the position of one or more of the sleeves by some remote control system to vary the wall thickness as desired, and, more preferably, in accordance with a pre-programmed control scheme.

As a further feature of the present invention, there may be a gas pressure that is established and maintained at the die face so that the tubing extruded therefrom does not immediately collapse while the tubing is being cooled and has the time to set. The set gas pressure can, with the use of the present invention, be varied in accordance with particular dimension of the mandrel, that is, as the mandrel is enlarged to greater dimensions, the pressure established within the tubing is increased to maintain that tubing inflated and to prevent it from collapsing since the tubing wall is thinner and additional pressure is required to maintain the tubing in the desired condition and to prevent its collapse.

Thus, the control system for the pressure controls the pressure in accordance with the dimensions of the mandrel or, in the preferred embodiment, the position of each of the sleeves. It is noted that an alternative to the presence of a positive pressure provided to the interior of the tubing, there may be a vacuum tank that produces a negative pressure that is applicable to the exterior of the tubing and either method can be used to prevent the collapse of the tubing These and other features and advantages of the present invention will become more readily apparent during the following detailed description taken in conjunction with the drawings herein.

BRIEF DESCRIPTION OF THE DRAWINGS

FIG. 6 is a perspective view of the sleeves of the present invention;

FIG. 7 is a schematic view of the sleeves of FIG. 6 in their operative, telescoping positions; and FIG. 8 is a schematic view of the sleeves of FIG. 6 and showing motive systems adapted to move the sleeves.

DETAILED DESCRIPTION OF THE INVENTION

Figure 1:
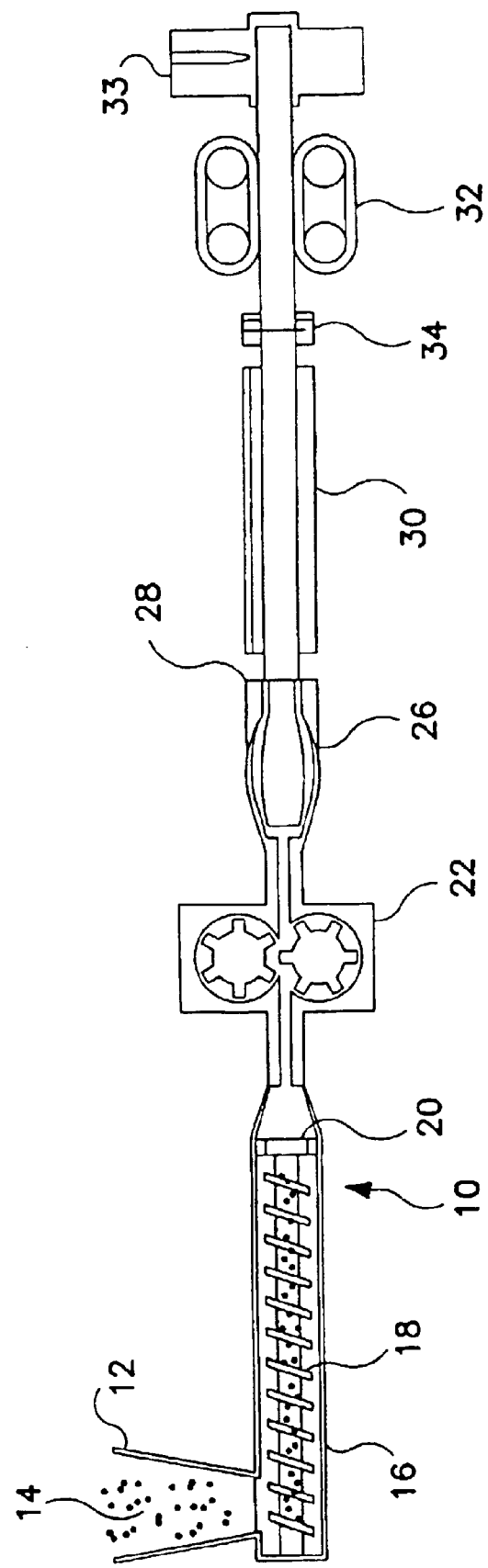
FIG. 1 is a schematic view of a typical extrusion process.

Referring now to FIG. 1, there is shown a schematic view of a typical extruder apparatus 10 that can be used in carrying out the present invention. As is conventional in the extrusion process, there is a hopper 12 that contains a reservoir of the material 14 to be extruded. The material from the hopper 12 descends downwardly via a gravity feed into the extruder barrel 16 where the material is progressed forwardly by a spiral screw 18 through a breaker plate 20. A gear pump 22 may be used to force the material 12 through the extrusion head 26 where the extruded form, such as a tubing, emerges from the die face 28, that is, the end of the extrusion head 26 and which is in a plane that is generally at a right angle to the flow of the extruded material.

Depending upon the particular material being extruded, the material may be heated to flowing temperatures if the material is a thermoplastic material or, alternatively, if a thermosetting material, the material can be cooled as extruded.

In any event, after the tubing has been extruded from the extrusion head 26, there is a water bath 30 through which the extruded tubing is drawn by means of a puller 32 so that the extruded tubing is cooled to achieve a permanent set. Finally, the extruded tubing passes by a cutter 33 that cuts the length of tubing desired by the user.

As will be later explained, there is also present a pressure system to establish and maintain a pressure in the interior of the extruded tubing so that the tubing does not collapse during the progress of the tubing as it passes through the water bath 30 until the tubing is sufficiently rigid to maintain itself. There also may be a laser 34 or other measuring device to measure the outside dimensions of the tubing.

Figure 2:
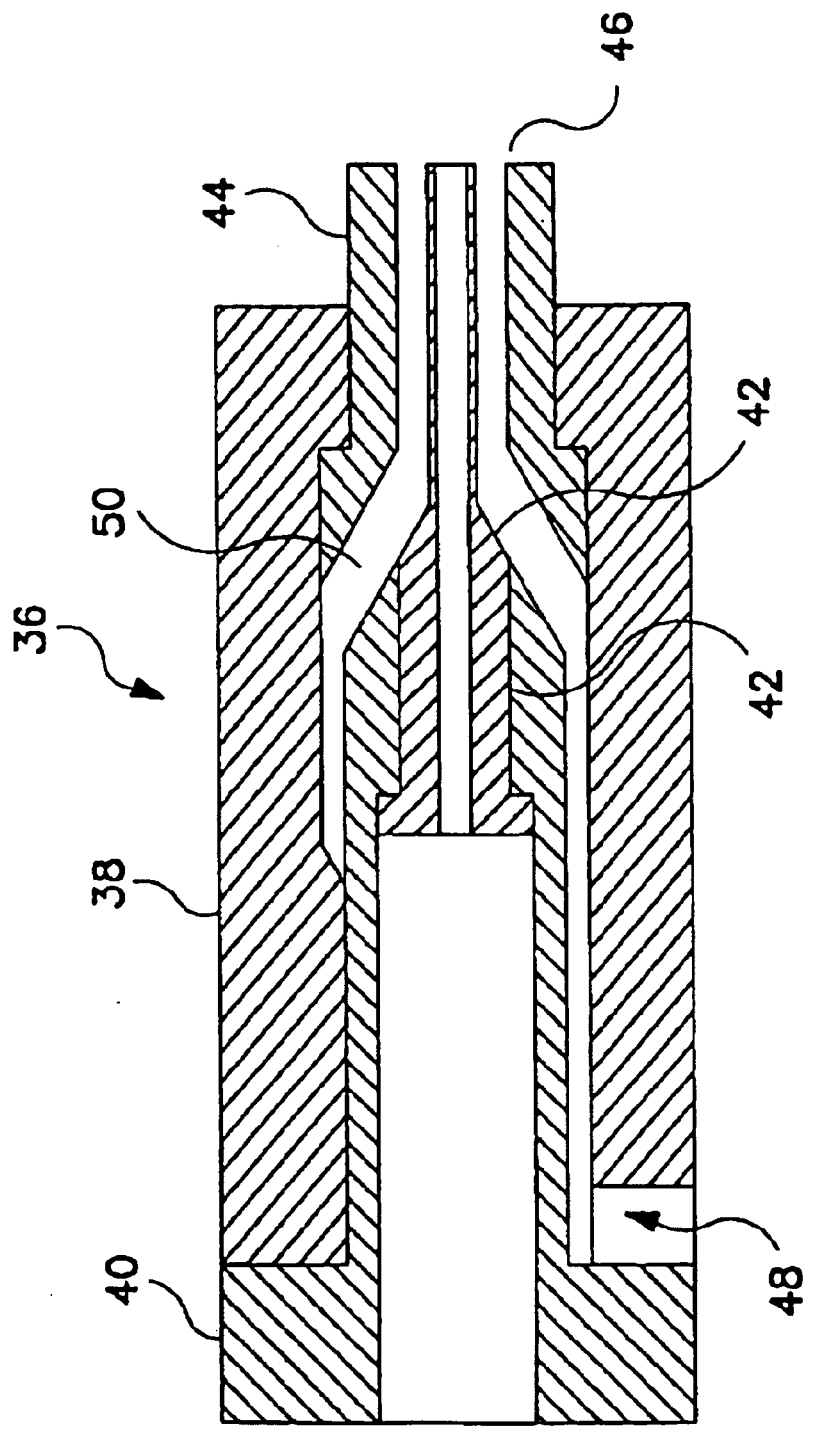
FIG. 2 is a cross-section view of a typical prior art extrusion head.

Turning now to FIG. 2, there is shown a cross-sectional view of a typical prior art extrusion head 36. As can be seen, the extrusion head 36 includes a crosshead body 38 having a helicoid 40 which helps to direct the flow of the material. A mandrel 42 fits into the helicoid 40 and a die 44 and the mandrel 42 extend outwardly from the crosshead body 38 to terminate at a die face 46 which is a face that is formed in a plane that is generally at a right angle to the flow of an extrudable material from the die face 46. The material to be extruded enters into the crosshead body 38 by means of a flow inlet 48 and passes in the space 50 between the mandrel 42 and the die 44, such that the outer surface of the extruded material is established by the inner surface of the die 44 and the inner surface of the extruded material is established by the exterior surface of the mandrel 42.

Accordingly, the relative location of the die 44 and the mandrel 42, governs the inner and outer surfaces of the extruded material. If the material is being extruded into, for example, a hollow, cylindrical tube, the outer diameter of the tubing is established by the inner surface of the die 44 and the inner diameter of the tubing is determined by the outer diameter of the mandrel 42. Obviously, by having the mandrel 42 or the die 44 of differing configurations, the outer peripheral configuration of the tubing can be square, rectangular, oval, hexagonal or other desired peripheral configuration. In addition, the wall thickness of the extruded tubing is determined by the space between the die 44 and mandrel 42 at the die face 46.

Figure 3:
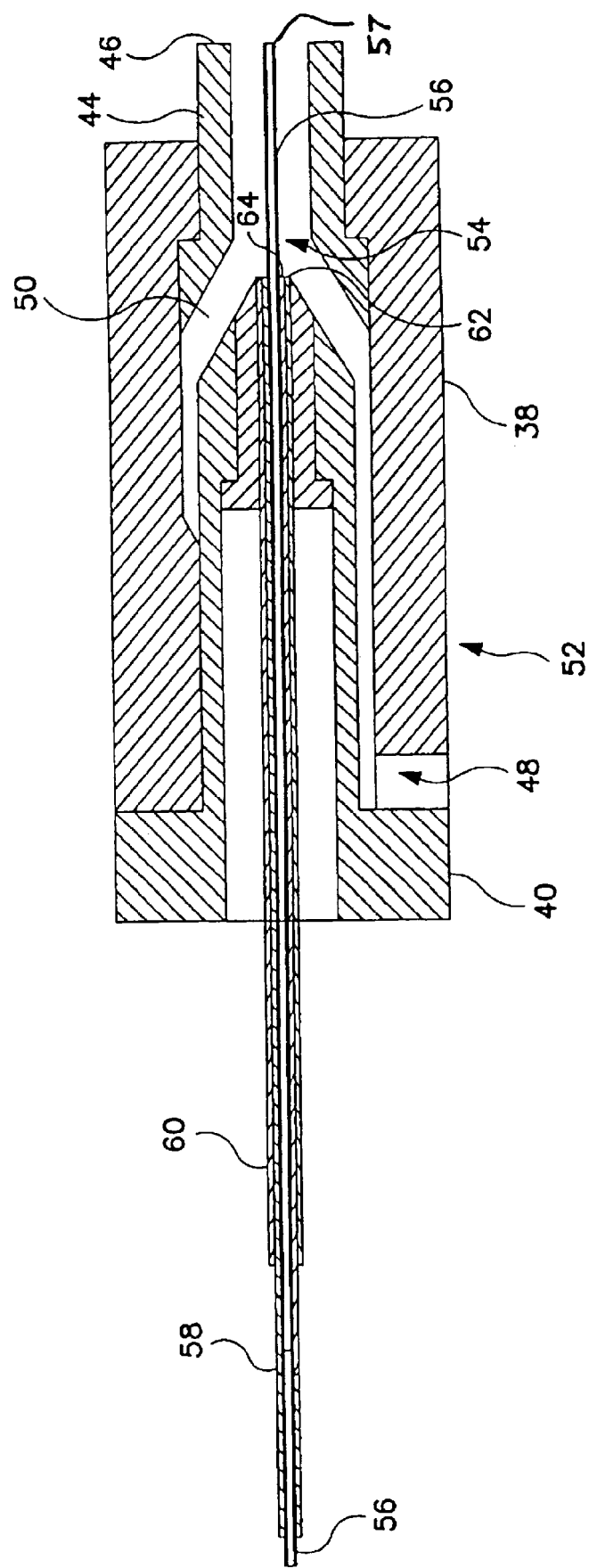
FIG. 3 is a cross-sectional view of an extrusion head constructed in accordance with the present invention and having a plurality of sleeves.
Figure 4:
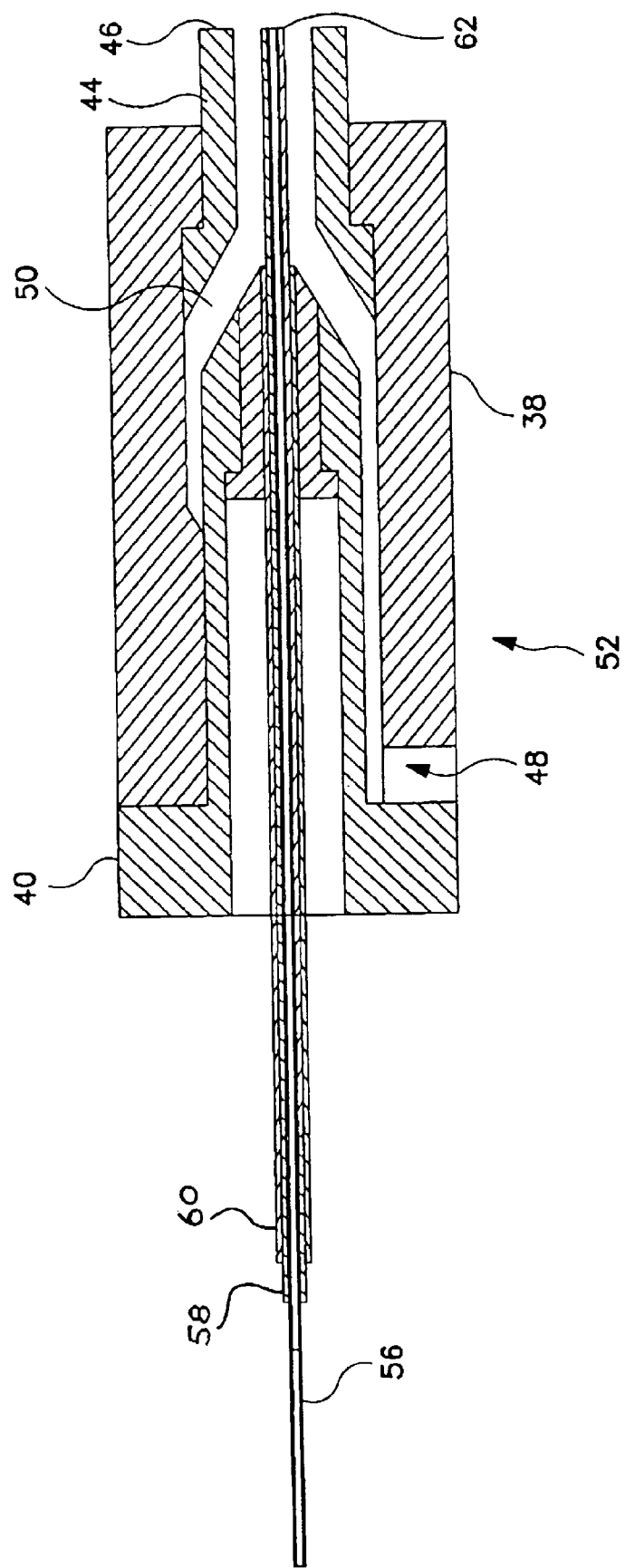
FIG. 4 is cross-sectional view of an extrusion head of FIG. 3 with the sleeves in an alternative position.
Figure 5:
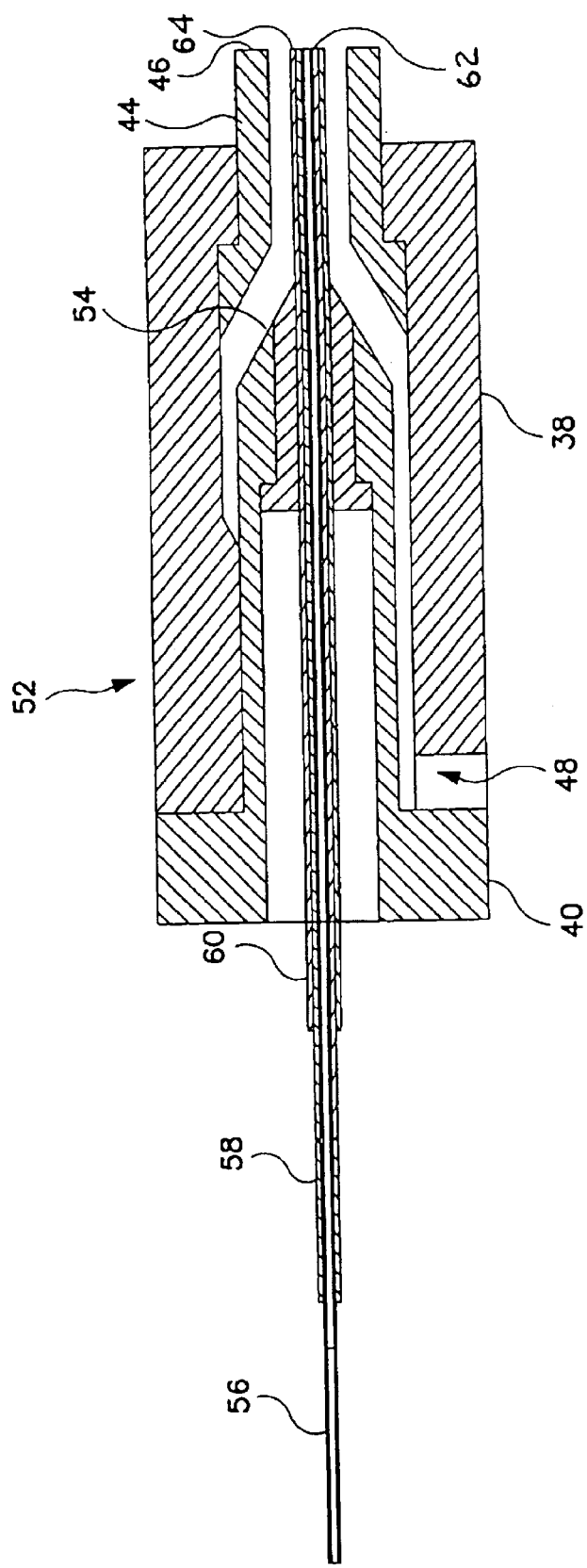
FIG. 5 is a cross-sectional view of an extrusion head of FIG. 3 having the sleeves in a still further alternative position.

Turning now to FIGS. 3–5, there are shown cross-sectional views of an extrusion head 52 constructed in accordance with the present invention. Taking first FIG. 3, it can be seen that the mandrel 54 is a specially designed mandrel and comprises a core 56 that can be mounted so as to be in a fixed position relative to the crosshead body 38. Other of the components shown in FIGS. 3–5 are the same as described with respect to FIG. 2 and have been given the same identification numbers as they carry out the same functions in the same manner. Therefore, the components and features include the crosshead body 38, helicord 40, die 44, die face 46, flow inlet 48 and a space 50. As will be seen, the space 50 does have a changing function in accordance with the present invention as does the specially constructed mandrel 54.

As such, in FIG. 3, the mandrel 54 comprises a core 56 that can be non-movably mounted within the crosshead body 38 and has a distal end 57 that extends to the die face 46 of the extrusion head 52 and therefore establishes the internal diameter of a tubing extruded from the die face 46. Since the core 56 is fixed with respect to the crosshead body 54, it will be seen that the core 56 establishes the smallest internal dimensions for the hollow tubing extruded therefrom, and, of course, if the tubing is circular, the smallest dimension will be the smallest inner diameter.

As will also be seen, however, in FIG. 3, there are a pair of sleeves, namely, an inner sleeve 58 and an outer sleeve 60 that telescope over the core 56 and can slide thereover. The inner sleeve 58 has a smaller outer dimension than the outer sleeve 60 in order to provide the telescoping relationship and, again, the sleeves 58, 60 may have any of a wide variety of outer configurations and shapes and sizes depending upon the particular tubing being extruded. In addition, as will now be appreciated, while only two sleeves 58, 60 are shown in FIGS. 3–5, there can be a lesser number or greater number of such sleeves in the spirit of the present invention.

In any event, the inner sleeve 58 slides along the outer surface of the core 56 and, correspondingly, the outer sleeve 60 slides along the outer surface of the inner sleeve 58 in a telescoping arrangement. As shown in FIG. 3, both of the sleeves 58, 60 have their distal ends 62, 64 respectively, displaced away from the die face 46 so that, in the positions shown in FIG. 3, the sleeves 58, 60 do not have any influence upon the inner dimensions of the extruded tubing.

In FIG. 4, however, it can be seen that the inner sleeve 58 has been moved from the retracted or displaced position of FIG. 3 to an extended position where the distal end 62 of the inner sleeve 58 is located at the die face 46 and therefore does determine the inner dimensions of the extruded tubing.

As can be understood, by moving the inner sleeve 58 from its retracted position of FIG. 3 to the extended position of FIG. 4, the inner dimension of the extruded tubing, that is, the inner diameter if a circular tubing is being produced, is increased. Accordingly, since the outer dimensions of the extruded tubing has not changed, the wall thickness of the extruded tubing has consequently been reduced. The reduction of the wall thickness can be abrupt such as when the inner sleeve 58 is moved rapidly from its retracted position to the extended position, or the change in the wall thickness can be gradual where the inner sleeve 58 is moved at a slower speed from the retracted to the extended positions.

Thus, the slope of the changes in the wall thickness can be controlled by the user in accordance with the desired end product tubing profile by controlling the speed of movement of the inner sleeve 58 between its retracted and extended positions and the reverse is equally true, when the inner sleeve 58 is moved back from its extended position to its retracted position of FIG. 3 so that the wall thickness can again be increased at whatever slope is desired by the user in creating the end product.

Taking now FIG. 5, there is shown a cross-sectional view of the extrusion head 52 shown with the outer sleeve 60 in its extended position such that the distal end 64 of the outer sleeve 60 is in the die face 46 and therefore the inner dimensions of the extruded tubing are established by the outer dimensions of the outer sleeve 60, the outer dimensions of the extruded tubing still being the same as the inner dimensions of the die 44. Therefore, the wall thickness of the extruded tubing has again been thinned over the FIG. 2 positions of the sleeves 58, 60 at the control of the user and, again, the control over the rate of the advancement or retraction of the outer sleeve 60 can be used to shape the inner profile of the extruded tubing.

In the movement of the inner and outer sleeves 58, 60, it should be noted that the movement of the sleeves 58, 60 should be carried out in a sequential manner, that is, the inner sleeve 58 is advanced to the extended position first and then as it is desired to further narrow the wall thickness of the extruded tubing, the outer sleeve 60 can then be advanced and the same is true of the withdrawal of the sleeves 58, 60 back to their retracted positions, i,e, the outer sleeve 60 is retracted first and then the inner sleeve 58 is retracted so that the sleeves 58, 60 are moved in a sequential order determined by the outer dimensions of the particular sleeve with the smaller of the sleeves being first moved from the retracted to the extended position and the larger sleeve being moved first from the extended position to the retracted position.

The sequence of motion is carried out even if there are more than two sleeves and would be applicable to any number of multiple sleeves used with the present invention.

Turning now to FIGS. 6A, 6B and 6C, there are shown, schematic views illustrating the use of multiple or a plurality of sleeves in accordance with the present invention. In FIG. 6A the core 56 is shown and is the innermost component of the mandrel 54 of FIGS. 3–5. As also can be seen there is a opening 66 that passes through the core 56 and which will be later explained for its use to produce a pressure within an extruded tubing to prevent the tubing from collapsing. In FIG. 6B, the inner sleeve 58 is shown positioned in telescoping arrangement over the core 56 and the distal end 62 of the inner sleeve 58 is located at the die face 46 where the outer dimensions of the inner sleeve 58 determine the inner dimensions of the extruded tubing (FIG. 5).

Next, in FIG. 6C, there is shown the core 56, the inner sleeve 58 and the outer sleeve 60 of the extrusion head 52, all telescoped together with the inner and outer sleeves 58, 60 in the extended positions with the distal ends 62 and 64, respectively, located at the die face 46 (FIG. 5) so that the inner dimensions of the extruded tubing is determined by the outer dimensions of the outer sleeve 60.

Turning next to FIG. 7, there is shown a schematic view of a set up for the present invention and basically illustrates the components of the mandrel 54. The core 56 is held in a fixed position within the extrusion head and that mounting is schematically shown by the clamp 68. There is also a gas fitting 70 at the proximal end 72 of the core 56 and, as explained, the gas fitting 70 is adapted to be affixed to a regulated and controlled source of gas to establish and maintain a controlled gas pressure at the distal end 74 of the core 56. Thus, there is also a gas pressure controller 76 that is used to control the pressure of the gas at the distal end 74 of the core 56. That gas pressure controller 76 can operate off various inputs, one of which being the location of the inner and outer cylinders 58, 60 as will be explained.

Turning finally to FIG. 8, there is shown a schematic view of the inner and outer sleeves 58, 60 and also showing the motive means or mechanism that can be used to move each of the sleeves 58, 60 between their extended and retracted positions. Thus, taking the outer sleeve 60 first, there can be a clamp 78 that affixes the outer sleeve 60 to a bracket 80 and that bracket 80 moved by a first motive means 82. As such, the first motive means 82 can be a linear motor 84 that is connected to the bracket 80 and moved by a lead screw 86. The first motive means 82 can be any means of providing motion to the bracket 80 and, of course, the outer sleeve 60, and can include a pneumatic system, a hydraulic system or some other type of motive means or system that is effective to slide the outer sleeve 60 between the retracted and extended positions.

In a similar manner, there is a second motive means 88 that moves the inner sleeve 58 in the same manner as the first motive means 82 and, again, may comprise a linear motor 90 that acts through a lead screw 92 to move the inner sleeve 58 by moving bracket 94 affixed to the inner sleeve 58 by a clamp 96. Therefore, as can be seen, the first motive means 82 and the second motive means 88 serve to move, individually, the inner and outer sleeves 58, 60 and each can be operated independently of the other and can move at different speeds depending upon the desired internal profile of an extruded tubing.

As noted, there is also a control system to establish and maintain a predetermined pressure within the tubing being extruded and that pressure is controlled by the gas pressure controller 78. The purpose of the gas pressure is to prevent the newly extruded tubing from collapsing while it is being cooled and eventually set and thereby strengthened. In the preferred embodiment, the gas pressure is established and then changed in accordance with the wall thickness of the extruded tubing, thus, as the mandrel dimensions get larger, the wall thickness becomes smaller and additional pressure is needed to maintain the wall tubing and prevent its collapse. The reverse is, of course, also true for the wall thickness as it gets larger, that is, less gas pressure is required within the larger wall thickness extruded tubing.

Therefore, there may be a feedback system that changes the set gas pressure established by the gas pressure controller 78 based upon the outer dimensions of the mandrel 54 (FIGS. 3–5). Accordingly, one such means of providing the necessary feedback can be by means of position sensors 98, 100 that sense the position of the inner and outer sleeves 58, 60 respectively so that the gas pressure controller 76 can receive the information via communication lines 104 and adjust the gas pressure accordingly.

As an example, when the inner sleeve 58 is moved to its extended position, the position sensor 98 can sense that the inner sleeve 58 has reached its extended position and therefore recognizes that the wall thickness of the extruded tubing has been narrowed. That information is provided to the gas pressure controller via the communication line 104 so that the pressure is then raised.

Obviously, the pressure can be lowered if the wall thickness is again thickened or increased by the reverse process. In the event some mechanism other than sleeves is used to change the dimensions of the mandrel 54 (FIGS. 3–5), other means can be used to change the gas pressure within the extruded tubing based upon the outer dimensions of the mandrel and/or the wall thickness of the extruded tubing.

Those skilled in the art will readily recognize numerous adaptations and modifications which can be made to the extruder and method of extruding tubing of the present invention which will result in an improvement, yet all of which will fall within the scope and spirit of the present as defined in the following claims. Accordingly, the invention is to be limited only by the following claims and their equivalents.

We claim:

1. An extruder apparatus for producing a length of hollow tubing, said apparatus comprising an extruder barrel for containing a material to be extruded, a extrusion head having a die face, means to move the material from said extruder barrel through said extrusion head and outwardly through said die face, said extrusion head having a central mandrel and having an outer die surrounding said central mandrel and forming a space between said central mandrel and said outer die for passage of the material though said extrusion head to form a hollow extruded tubing having inner dimensions determined by the outer dimensions of said mandrel, means to vary the outer dimensions of said mandrel so as to vary the inner dimensions of a tubing extruded from said extrusion head, said extruder apparatus further including a pressure means to provide a predetermined pressure within the tubing as it is extruded from said extrusion head, and a pressure controller adapted to control the level of pressure provided within the tubing to maintain the inner dimension of the tubing and prevent the tubing from collapsing.

2. An extruder apparatus as defined in claim 1 wherein said mandrel comprises a inner core having predetermined dimensions and at least one sleeve surrounding said inner core, said at least one sleeve being movable between a retracted position wherein said sleeve is displaced away from said die face and an extended position wherein said at least one sleeve is within said die face and determines the inner dimensions of tubing extruded from said extrusion head.

3. An extruder apparatus as defined in claim 2 wherein said extrusion head includes a motive system for moving said at least one sleeve between said retracted and said extended positions.

4. An extruder apparatus as defined in claim 3 wherein said at least one sleeve comprises a plurality of sleeves and said motive system comprises a plurality of motive mechanisms adapted to individually move each of said plurality of sleeves between said retracted and said extended positions.

5. An extruder apparatus as defined in claim 1 wherein said pressure controller controls the level of the pressure based upon the outer dimensions of the mandrel.

6. An extruder apparatus as defined in claim 5 wherein said pressure controller increases the pressure within said tubing as the outer dimensions of said mandrel increases.

7. An extruder apparatus as defined in claim 2 wherein said pressure controller controls the level of pressure based upon the position of said at least one sleeve.

8. An extrusion head for extruding a multi-lumen tubing, said extrusion head comprising a plurality of mandrels and an outer die surrounding each of said plurality of mandrels and forming a space between each of said plurality of mandrels and each outer die for passage of material though each of said spaces and outwardly through a die face to form a hollow extruded tubing having a plurality of lumens with each of said lumens having inner dimensions determined by the dimensions of one of said plurality of mandrels, means to vary the dimensions of each of said plurality of mandrels so as to vary the individual inner dimensions of each of said plurality of lumens in the tubing extruded from said extrusion head.

9. An extruder apparatus for extruding a multi-lumen tubing, said apparatus comprising an extruder barrel for containing a material to be extruded, an extrusion head having a die face, means to move the material from said extruder barrel through said extrusion head and outwardly through said die face, said extrusion head having a plurality of mandrels and having an outer die surrounding each of said plurality of mandrels and forming a space between each of said plurality of mandrels and each outer die for passage of the material though said extrusion head to form a hollow extruded tubing having a plurality of lumens, each of said lumens having inner dimensions determined by the outer dimensions of each of said plurality of mandrels, means to vary the outer dimensions of each of said plurality of mandrels so as to vary the inner dimensions of each of the plurality of lumens within a multi-lumen tubing extruded from said extruder apparatus.

* * * * *